(12) United States Patent
Zhou et al.

(10) Patent No.: US 11,160,943 B2
(45) Date of Patent: Nov. 2, 2021

(54) CUSHION FOR BREATHING MASK AND BREATHING MASK

(71) Applicant: BMC Medical Co., Ltd., Beijing (CN)

(72) Inventors: Mingzhao Zhou, Beijing (CN); Yajie Wang, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 218 days.

(21) Appl. No.: 15/744,803

(22) PCT Filed: Dec. 23, 2016

(86) PCT No.: PCT/CN2016/111814
§ 371 (c)(1),
(2) Date: Jan. 14, 2018

(87) PCT Pub. No.: WO2017/107991
PCT Pub. Date: Jun. 29, 2017

(65) Prior Publication Data
US 2018/0207384 A1    Jul. 26, 2018

(30) Foreign Application Priority Data

Dec. 24, 2015   (CN) .......................... 201510993225.6

(51) Int. Cl.
*A61M 16/06*     (2006.01)
(52) U.S. Cl.
CPC .... *A61M 16/0622* (2014.02); *A61M 16/0616* (2014.02); *A61M 16/0633* (2014.02); *A61M 16/0683* (2013.01); *A61M 2205/0216* (2013.01)

(58) Field of Classification Search
CPC .......... A61M 16/06–0655; A61M 2016/0661; A61M 16/0683; A61M 2205/0216;
(Continued)

(56) References Cited

U.S. PATENT DOCUMENTS

| | | | | |
|---|---|---|---|---|
| 2,133,699 A | * | 10/1938 | Heidbrink | A61M 16/06 128/206.24 |
| 3,330,273 A | * | 7/1967 | Bennett | A61M 16/0622 128/206.26 |

(Continued)

FOREIGN PATENT DOCUMENTS

| CA | 2938398 A1 | 9/2015 |
|---|---|---|
| CN | 103917267 A | 7/2014 |

(Continued)

*Primary Examiner* — Elliot S Ruddie
(74) *Attorney, Agent, or Firm* — Bayramoglu Law Offices LLC

(57) ABSTRACT

A cushion for a breathing mask and a breathing mask. The cushion includes a connection portion for connecting to a frame or an elbow assembly of the breathing mask; a face contact portion for getting in contact with the face of a patient, wherein the face contact portion is formed by a thin membrane; and a support portion which is connected between the connection portion and the face contact portion, wherein the face contact portion has an outwardly extending portion which extends from the support portion to the exterior of the cushion and an inwardly extending portion which extends from the outer circumference side of the outwardly extending portion to the interior of the cushion in at least partial area.

14 Claims, 12 Drawing Sheets

(58) Field of Classification Search
CPC ............... A63B 33/00–004; A61F 9/02; A61F 2009/021; A61F 9/06–068; B63C 11/12; A62B 7/00–14; A62B 18/00–08
USPC ............ 128/206.21, 206.22, 206.24, 206.26, 128/206.12; 2/6.3, 426–454, 909
See application file for complete search history.

(56) References Cited

U.S. PATENT DOCUMENTS

| | | | | |
|---|---|---|---|---|
| 3,330,274 | A * | 7/1967 | Bennett | A62B 18/025 128/206.26 |
| 2003/0196656 | A1 | 10/2003 | Moore et al. | |
| 2011/0162654 | A1 * | 7/2011 | Carroll | A61M 16/06 128/206.21 |
| 2013/0008445 | A1 | 1/2013 | Boussignac | |
| 2015/0157824 | A1 * | 6/2015 | Ho | A61M 16/0622 128/206.24 |
| 2017/0312468 | A1 * | 11/2017 | Formica | A61M 16/0825 |
| 2017/0333657 | A1 * | 11/2017 | Stephenson | A61M 16/0605 |

FOREIGN PATENT DOCUMENTS

| | | | |
|---|---|---|---|
| CN | 105148375 | A | 12/2015 |
| CN | 105413035 | A | 3/2016 |
| CN | 205268787 | U | 6/2016 |
| FR | 2988003 | B1 | 9/2014 |
| WO | 2004022146 | A1 | 3/2004 |
| WO | 2013156910 | A1 | 10/2013 |
| WO | 2014020468 | A1 | 2/2014 |

* cited by examiner

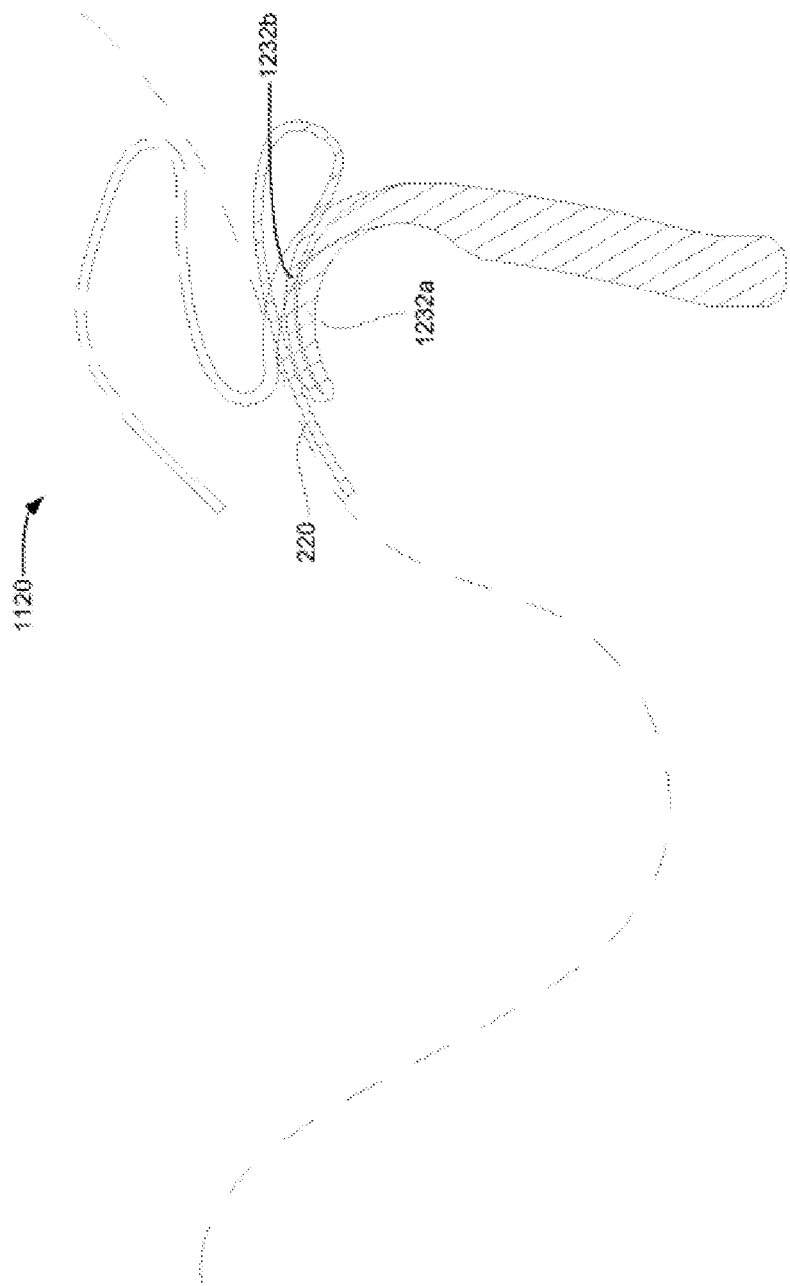

CUSHION FOR BREATHING MASK AND BREATHING MASK

CROSS-REFERENCE TO RELATED APPLICATIONS

This application is the national stage entry of International Application No. PCT/CN2016/111814, filed on Dec. 23, 2016, which claims the benefit of priority from Chinese Patent Application No. CN201510993225.6, filed on Dec. 24, 2015, the entire contents of which are incorporated herein by reference.

TECHNICAL FIELD

The disclosure relates to the technical field of breathing masks, and specifically to a cushion for a breathing mask and a breathing mask.

BACKGROUND

Wearing a breathing mask as a means of non-invasive ventilation therapy has been widely applied to the treatment of the OSA (Obstructive Sleep Apnea), COPD (Chronic Obstructive Pulmonary Disease), etc. The breathing mask is connected to a ventilator through a pipe, delivering CPAP (Continuous Positive Airway Pressure) or varying positive airway pressure to the air duct of a patient, for example, bi-level positive airway pressure that varies along with the breaking cycle of the patient or automatic adjusting positive airway pressure that varies along with the monitored conditions of the patient. The pressure supporting therapy is also usually applied to diseases such as OSA, UARS (Upper Airway Resistance Syndrome) and CHF (Congestive Heart-Failure).

An existing breathing mask usually includes a frame and a cushion. When the breathing mask is fixed on the face of a patient through a fixture, for example a headgear, the cushion is in contact with the face of the patient, and forms a sealed cavity with the face of the patient. Existing ventilation therapy usually takes a long time, and the patient usually needs to wear the breathing mask for the whole night. On the above basis, the breathing mask should be as comfortable as possible, and the sealing needs to be as stable and firm as possible. The two requirements are all involved with the cushion. If the patient does not feel good when wearing the breathing mask, the patient may refuse the treatment. If the tightness is insufficient, the air may leak. On the one hand, if the pressure is lower than the treatment value, the treatment fails; on the other hand, the leaking air flow may impact the face of the patient, in particular, the sensitive region, bridge of the nose or eyes, and may cause discomfort, the leaking air flow will make the patient refuse the treatment.

Existing cushions are mainly classified into two types, double-membrane cushions and single-membrane cushions according to the structure. The double-membrane cushion usually includes a sealing unit with upper and lower layers, and a support unit. The defects of the double-membrane technology include complicated manufacturing, high cost and washing inconvenience, which are the advantages compared with the single-membrane cushion. However, the existing single-membrane cushion technologies have problems. On the one hand, the level of comfort is limited, on the other hand, it is easy to leak air flow. The single-membrane cushion refers to that the support unit is integrated with the sealing unit. The problem of sealing mainly depends on the stressed situation of the portion that is in contact with the face. If a firm sealing is required, the pressure on the contact between the cushion and the face should be increased, which may be achieved by tightening the headgear. This may result in that the contact stress on the face of the patient exceeds the bearing limits of the face, and further cause marks, red spots and even ulcers. On the contrary, reducing the stress applied on the face by the cushion may lead to air leakage, resulting in treatment failure.

SUMMARY

In order to solve the problems of sealing and level of comfort of the single-membrane cushion in the prior art, the disclosure provides a cushion for a breathing mask and a breathing mask with the cushion.

According to an aspect of the present disclosure, there is disclosed a cushion for a breathing mask, wherein the cushion comprises: a connection portion for connecting to a frame or an elbow assembly of the breathing mask; a face contact portion for getting in contact with the face of a patient, wherein the face contact portion is formed by a thin membrane; and a support portion connected between the connection portion and the face contact portion, wherein the face contact portion has an outwardly extending portion which extends from the support portion to the exterior of the cushion and an inwardly extending portion which extends from an outer circumference of the outwardly extending portion to the interior of the cushion in partial area.

Preferably, the inwardly extending portion has a high point, the inwardly extending portion is divided into a first inwardly extending portion which is connected with the outwardly extending portion and a second internal portion which is connected with the first inwardly extending portion at the high point which serves as the boundary; and by the effect of the face of the patient, the high point of the inwardly extending portion abuts against the support portion.

Preferably, by the effect of the face of the patient, the first inwardly extending portion and the outwardly extending portion form a closed air bag, while the first inwardly extending portion is tightly in contact with and seals the face of the patient to form a second sealing area; and by the effect on the face of the patient, the second inwardly extending portion warps toward the face of the patient and is in contact with and seals the face of the patient to form a first sealing area.

Preferably, the maximum thickness of the face contact portion is smaller than the minimum thickness of the support portion.

Preferably, the support portion comprises a pressure support portion and a contact support portion which are connected to each other, wherein the pressure support portion is connected to the connection portion, the pressure support portion forms a patient cavity of the cushion; and wherein the contact support portion is connected to the face contact portion, the contact support portion is a transition portion between the pressure support portion and the face contact portion, and by the effect of the face of the patient, the face contact portion abuts against the contact support portion.

Preferably, the pressure support portion and/or the contact support portion inclines towards the exterior of the cushion along the direction from the connection portion to the face contact portion.

Preferably, a longitudinal inclination angle of the pressure support portion is 3-15 degrees with respect to the pressure support portion.

Preferably, an internal circumferential surface of the contact support portion has a circular arc which projects towards the interior of the cushion.

Preferably, the contact support portion comprises a first contact support portion and a second contact support portion in at least a partial area; the first contact support portion extends towards the interior of the cushion from the pressure support portion, and the second contact support portion extends from the first contact support portion towards the exterior of the cushion to the face contact portion, to form a groove between the first contact support portion and the second contact support portion.

Preferably, by the effect of the face of the patient, the second contact portion is overlaid on the first contact support portion.

Preferably, the second contact support portion is formed by a thin membrane, or/and the thickness of the first contact support portion gradually decreases from the pressure support portion to the extension direction of the second contact support portion.

Preferably, the groove gradually opens towards the exterior of the cushion.

Preferably, the second contact support portion circularly bends from the first contact support portion such that the bottom of the groove is a circular bead.

Preferably, the connection portion comprises: a connection section connected to the breathing mask, wherein the transverse size of the connection section is smaller than the transverse size of the support portion; and a bent section, the bent section being connected between the connection section and the support portion.

Preferably, along the circumference direction of the cushion, the cushion comprises an upper area, a lower area, and a middle area which is connected between the upper area and the lower area, and the transverse width of the bent section gradually reduces from the upper area to the middle area and from the lower area to the middle area.

According to another aspect of the present disclosure, a breathing mask is provided, comprising: a frame, wherein a main body of the frame has an air delivery port which is connected to a bend tube; and a cushion according to the embodiments, the cushion being connected to the frame through the connection portion.

In the disclosure, the face contact portion of the cushion includes an outwardly extending portion which extends outward and an inwardly extending portion which extends inward, so that by the effect of the face of the patient, the inwardly extending portion of the face contact portion may abut against the support portion which plays a support role. In this way, a sealing point may be formed at the position of the abutted point and two sealing areas may be formed on two sides of the abutted point, thus ensuring a firm sealed state.

Moreover, in the disclosure, a thin membrane material is adopted to form the face contact portion to effectively fill in irregular or uneven areas of the face by the effect of the air pressure in a hollow cavity of the breathing mask, then ensuring reliable sealing. Therefore, in comparison with the prior art, the required support force may be smaller while the same sealing effect is achieved. In addition, due to the buffer effect of the face contact portion, even if the mask is moved during use, the relative movement between the support portion and the face contact portion occurs instead of the relative movement between the face contact portion and the face of the patient, thus the anti-movement performance is relatively high. Therefore, it can be seen that, the cushion provided in the disclosure is simply manufactured and conveniently washed, but what is more important is that the patient is safely and reliably provided with a firm seal on the face with a relatively small face contact force, thus minimizing the leak, improving the level of comfort and making the treatment process of the patient more relaxed.

A series of simplified concepts are introduced into the contents of the disclosure, and will be described in further detail in the section of the detailed description of the contents of the disclosure. The contents of the disclosure do not limit the key characteristics and necessary technical characteristics of the claimed technical solution, and do not define the protective scope of the claimed technical solution.

The advantages and characteristics of the disclosure are described in detail in conjunction with the attached drawings.

BRIEF DESCRIPTION OF THE DRAWINGS

The following attached drawings of the disclosure as a part of the disclosure are employed to explain the disclosure here. Implementation modes and descriptions thereof of the disclosure illustrated in the attached drawings are employed to explain the principle of the disclosure. Among the attached drawings.

DETAILED DESCRIPTION OF THE INVENTION

Figure 1:
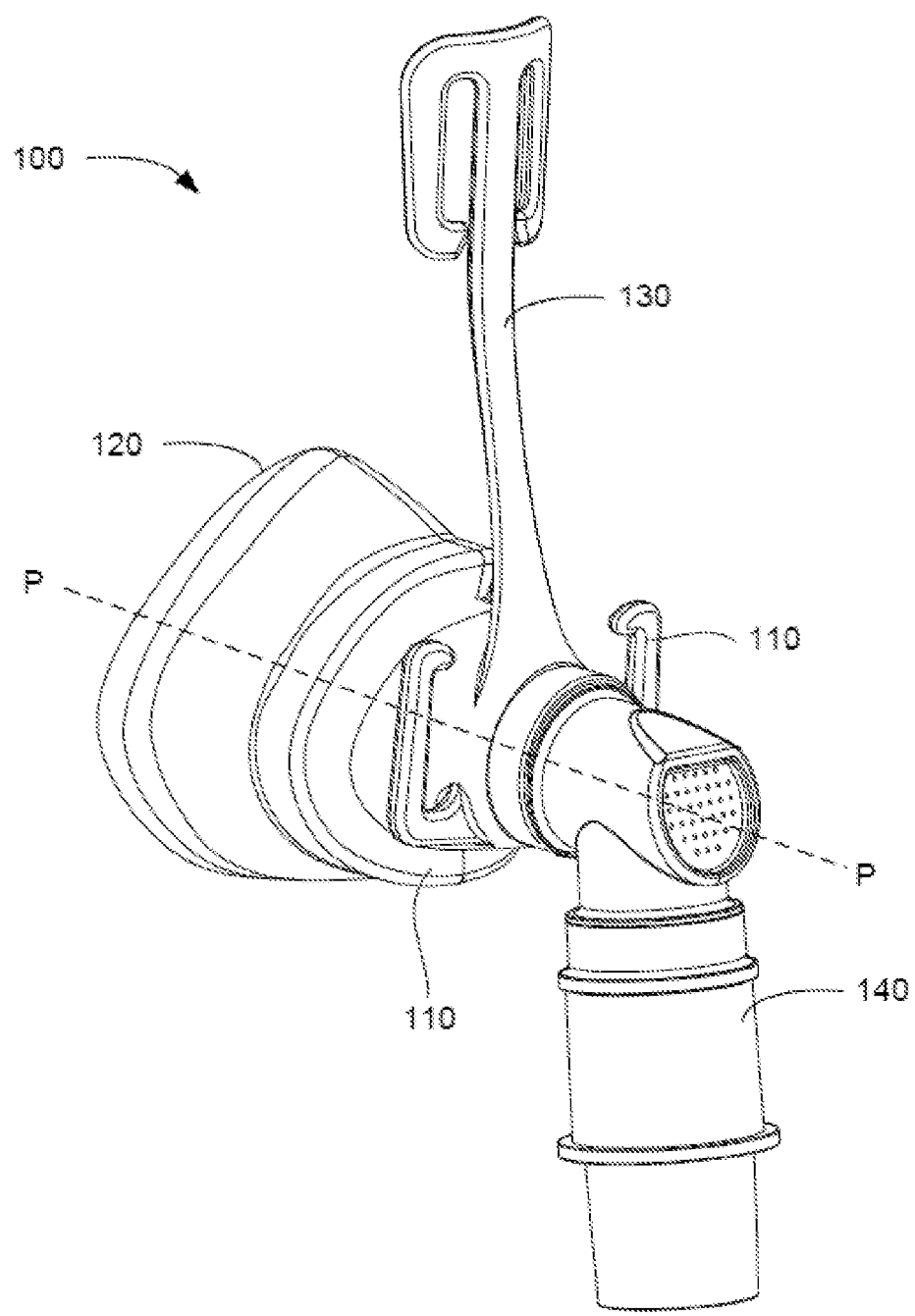
FIG. 1 is a three-dimensional view of a breathing mask in the first group of embodiments according to the disclosure.

In the description of the text below, a huge amount of details are provided to thoroughly explain the disclosure. However, those skilled in the art may understand that the following description merely illustrates the preferred embodiments of the disclosure, and the disclosure may be executed without one or more such details. Besides, in order to avoid confusion with the disclosure, some technical characteristics known in the art are not described in detail.

One objective of the disclosure is to provide a cushion for a breathing mask (hereinafter referred to as cushion). In order to accurately and completely explain the cushion, the breathing mask which adopts the cushion is briefly described first in the embodiment of the disclosure. It is understandable that, a nasal type breathing mask in the drawings is merely illustrative, and the application of the cushion provided in the embodiment of the disclosure is not limited to the nasal type breathing mask, but the oral-nasal type breathing mask or full-face type breathing mask.

Refer to FIG. 1, which is a three-dimensional view of a breathing mask in the first group of embodiments according to the disclosure. As shown in the three-dimensional view in FIG. 1, the breathing mask 100 may include a frame (also called mask body) 110, a cushion 120, a forehead support member 130 and an elbow assembly 140. In other not shown embodiments, the breathing mask 100 may not include one or two components, for example, not include the forehead support member 130.

The cushion 120 is installed on the frame 110. The frame 110 together with the cushion 120 may form a patient cavity for accommodating the nose or nose and mouth of the patient. The cushion 120 may also individually form the patient cavity. In this embodiment, the frame 110 may support the cushion 120 outside the cushion 120. The cushion 120 may be fixedly connected to or detachably connected to the frame 110. When in use, the cushion 120 is in contact with the face of the patient (including the cheeks, bridge of the nose, upper or lower part of the mouth, etc.) such that the patient cavity communicates with the nasal cavity or oral and nasal cavities of the patient. The frame 110 may be made of a rigid material or a flexible material. The cushion 120 is preferably made of a flexible material. The rigid material may be plastic, alloy, etc., and the flexible material may be silica gel, gel, foam, airbag, textile, etc. Preferably, the cushion 120 may be made of a flexible and deformable material, for example silica gel. In addition, the cushion 120 may also be made of other appropriate biocompatible materials. The cushion 120 may have elasticity after being manufactured. Viewed from the front face of the breathing mask 100, the shapes of the frame 110 and the cushion 120 are not limited to the approximately triangular shape as shown in FIG. 1, but also pyriform shape, trapezoid, etc. The frame 110 and the cushion 120 may also have any other shapes which are matched with the shape of the mouth and/or nose. Preferably, the cushion 120 may be manufactured with any integrated molding process, for example injection molding or blowing molding.

The frame 110 or the cushion 120 is provided with an air delivery port. An elbow assembly 140 is connected to the frame 110 or the cushion 120 through the air delivery port. A pressure support device (for example ventilator) is connected with the elbow assembly 140 through an air supply pipe (not shown in FIG. 1) such that air with a proper pressure is supplied into the patient cavity and then enters the patient airway. The air supplied to the patient may be any proper breathing air known in the prior art. The air supply pipe may be a corrugated hose frequently used in the ar. It is understandable that the embodiment of the disclosure does not limit the specific air delivery port.

Besides, the frame 110 may also be provided with fixing structures such as buckles and bandage rings, to connect a fixed component (not shown in FIG. 1). The fixed component plays the role of fixing the breathing mask 100 at a proper position on the face of the patient, and may be various existing headgear. The headgear may have a structure which is connected with the frame 110, for example a buckle, and a velcro strap. Further, in order to more firmly and comfortably fix the breathing mask 100 on the face of the patient, the breathing mask 100 may also include a forehead support member 130, and the forehead support member 130 abuts against the forehead of the patient when in use. The connection between the forehead support member 130 and the frame 110 may be a fixed or a detachable connection. The detachable connection embodiment may be executed with a buckle position. The forehead support member 130 may include a flexible contact portion. The forehead support member 130 may also have an adjusting portion to adjust the distance to the forehead and ensure adaption to different face types.

It should be explained that, the orientation terms in the disclosure, for example "front face," "rear face," "front," "rear," "upper," "lower," "left," "right," "external," "internal," etc., are all defined with respect to an observer who faces the patient who wears the breathing mask 100 and whose head is upright. In terms of the placement as shown in FIG. 1, the orientation terms are obtained by viewing the breathing mask 100 from the side where the elbow assembly 140 is installed. For example, the front face refers to the orientation which is obtained by observing the breathing mask 100 from the side where the elbow assembly 140 is installed; and the rear face refers to the orientation which is obtained by observing the breathing mask 100 from the side where the cushion 120 is installed.

The objective of the disclosure is to provide a new cushion, while other components included by the breathing mask 100 may be structures known in the art and therefore are not described in further detail here. A plurality of preferable embodiments of the cushion provided by the disclosure is described in detail below in conjunction with the attached drawings.

Figure 2:
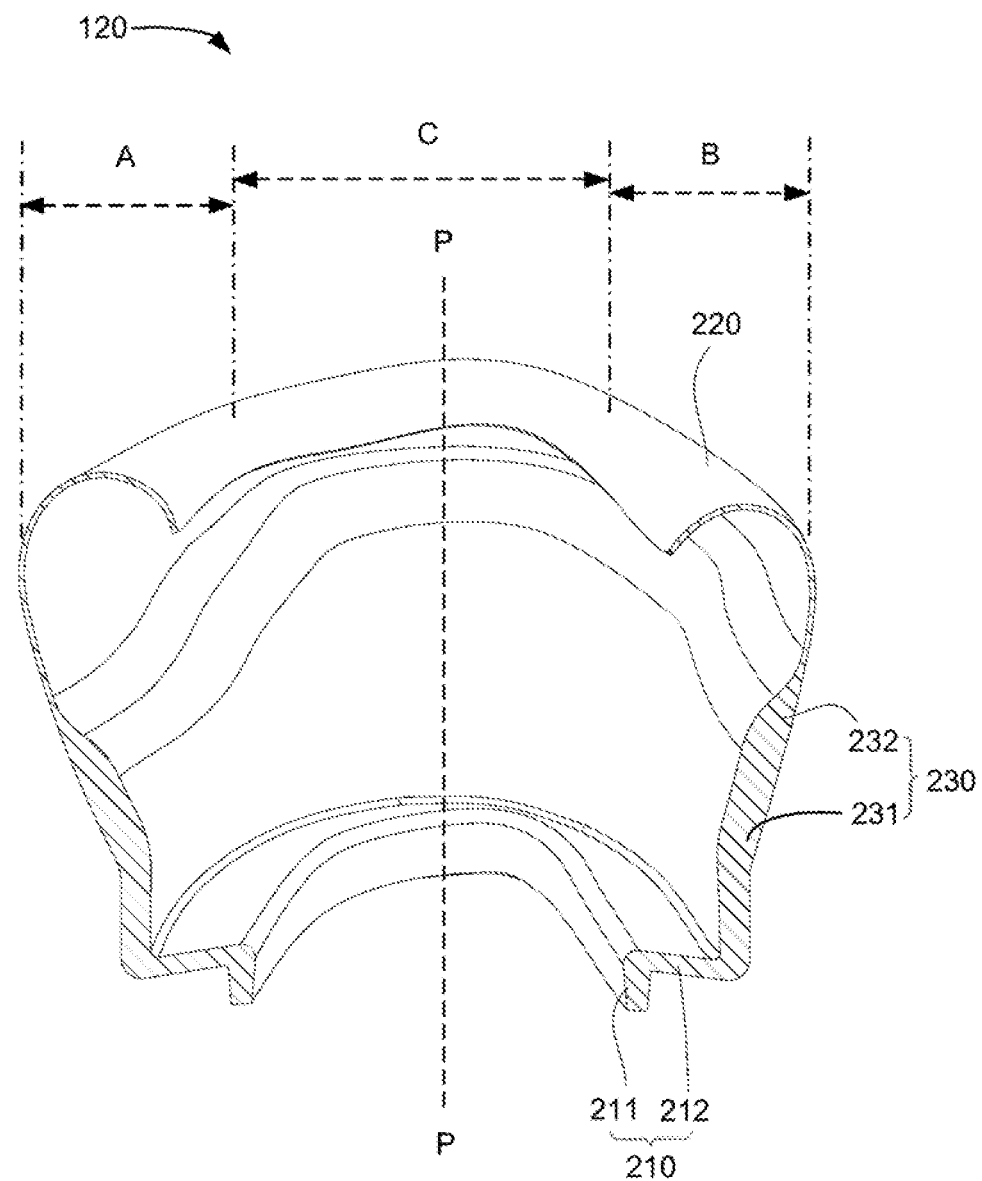
FIG. 2 is a sectional view of a cushion in the first group of embodiments according to the disclosure.
Figure 3:
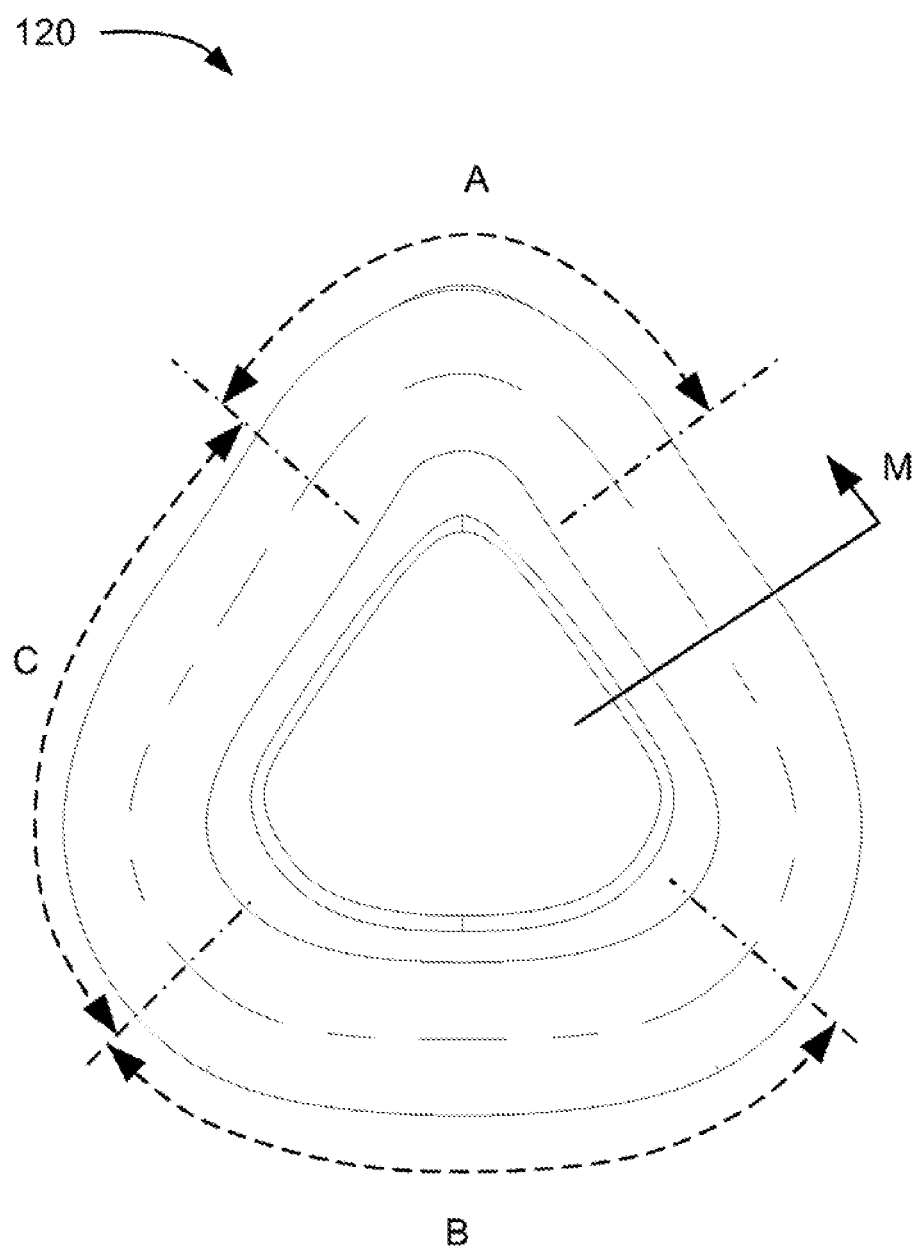
FIG. 3 is a rear view of the cushion in FIG. 2.
Figure 4:
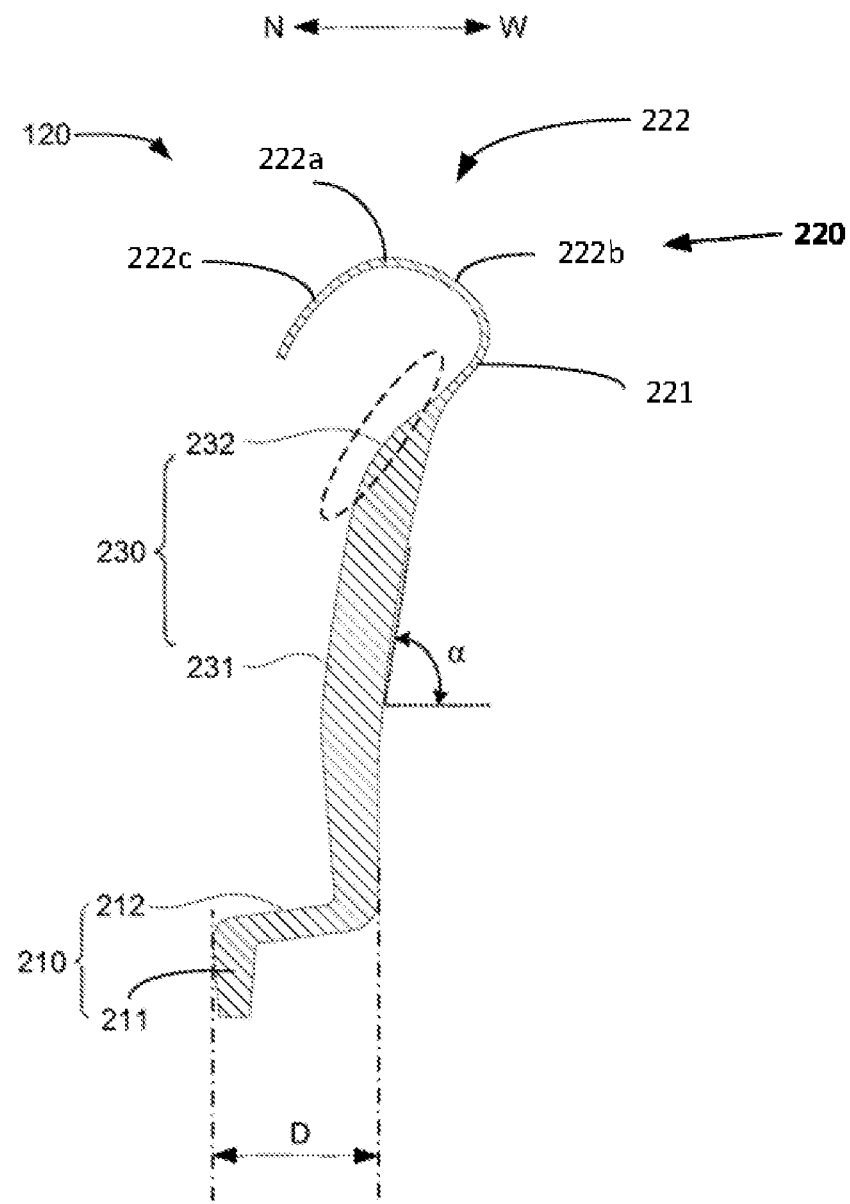
FIG. 4 is an sectional view of the cushion along the arrow M in FIG. 3.

FIG. 2 illustrates the sectional view of the cushion 120 obtained after the breathing mask as shown in FIG. 1 is sectioned by half; FIG. 3 illustrates a rear view of the cushion 120; and FIG. 4 is a sectional view obtained when the cushion 120 is sectioned along the arrow M as shown in FIG. 3. As shown in FIG. 2-4, the cushion 120 may include a connection portion 210, a face contact portion 220 and a support portion 230.

Figure 7:
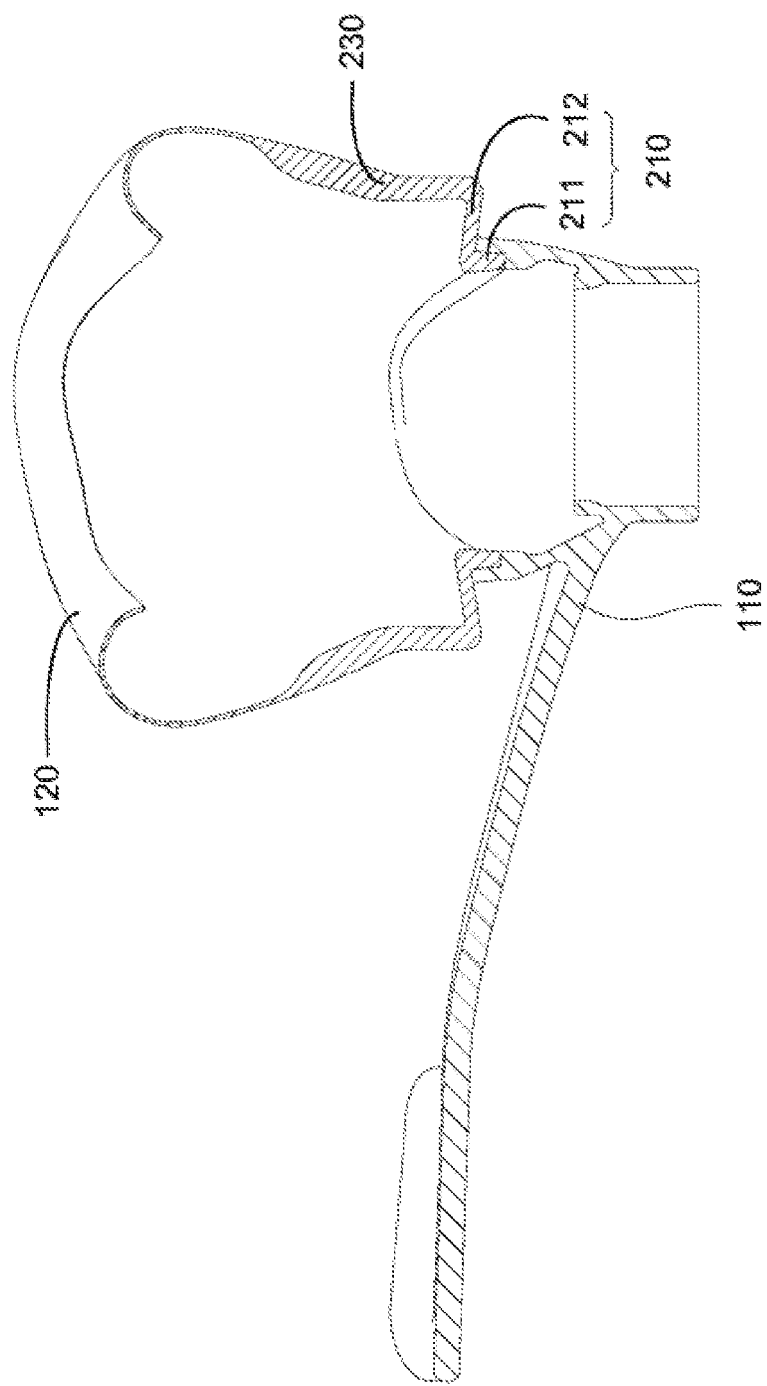
FIG. 7 is a longitudinal sectional view of a breathing mask in another embodiment in the first group of embodiments according to the disclosure, where the elbow assembly is removed.
Figure 8:
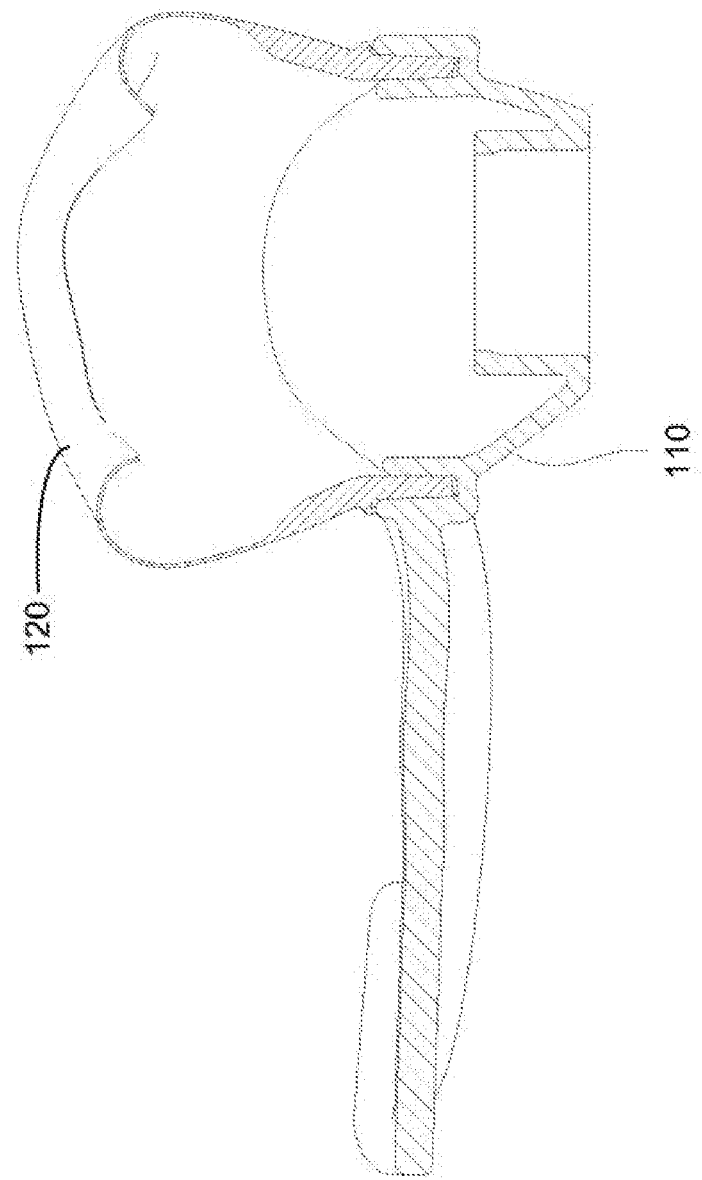
FIG. 8 is a longitudinal sectional view of a breathing mask in another embodiment in the first group of embodiments according to the disclosure, where the elbow assembly is removed.

The connection portion 210 is used for connecting to the frame 110 (see FIG. 1) or an elbow assembly of the breathing mask 100. The connection portion 210 and the frame 110 or the elbow assembly may be in a detachable connection, for example, a clearance fit (as shown in FIG. 8) or an interference fit. In FIG. 8, the cushion 120 may be clamped in the clearance of the frame 110 in the entire circumference. Optionally, the cushion 120 may be clamped in the clearance of the frame 110 or the elbow assembly at partial positions (for example positions corresponding to the bridge of the nose, upper lip and/or lower lip, etc.) of the circumference. The connection portion 210 and the frame 110 or the elbow assembly may be in detachable connection, for example adhesion connection (as shown in FIG. 7), or the two are molded one time by injection.

The face contact portion 220 and the connection portion 210 are arranged with respect to each other along the longitudinal direction of the cushion 120 (namely the extension direction of the central line P-P). The face contact portion 220 is used for getting in contact with the face of the patient. The face contact portion 220 is mainly used to form a seal with the face of the patient. The central line P-P is vertical to the face of the patient when the patient wears the breathing mask.

The support portion 230 is connected between the connection portion 210 and the face contact portion 220. The support portion 230 approximately extends along the extension direction of the central line P-P. On the one hand, the support portion 230 is used to form the patient cavity; and on the other hand, the support portion 230 is used to support the face contact portion 220.

The connection portion 210, the face contact portion 220 and the support portion 230 together form an annular cushion 120. The word "annular" refers to that the cushion 120 is connected end to end around the central line P-P, and does not limit the cushion 120 to be circular ring-shaped. In the embodiments in the drawings, the cushion 120 and the cushion 200 are approximately triangular. As mentioned above, the cushion 120 may also be pyriform shape, trapezoid shape, etc. when viewed from the front face, so the cushion 120 may also be shaped as an approximately pyriform loop or trapezoid loop. Based on the above definition, in this embodiment, the direction around the central line P-P is called the circumference direction of the cushion 120, and the direction which starts from the central line P-P and is vertical to the extension direction of the central line P-P is called the transverse direction of the cushion 120.

Along the circumference direction of the cushion 120, the cushion 120 may include an upper area A, a Lower area B and a middle area C, as shown in the preferable embodiment in FIG. 2-3. When in use, the upper area A of the cushion 120 is usually in contact with the bridge of the nose of the patient; and the lower area B of the cushion 120 is usually in contact with the upper part of the upper lip (nasal mask) of the patient or the lower part of the lower lip (oral and nasal mask). The middle area C is connected between the upper area A and the lower area B. The middle area C may include a left portion and a right portion that is respectively in contact with the left and right cheeks of the patient. The bridge of the nose, the upper lip and the lower lip are relatively sensitive stress areas with respect to the cheeks. In this embodiment of the disclosure, the different structures are designed for different areas such that it is more comfortable to wear the breathing mask and better sealing is obtained.

The face contact portion 220 may be formed by a thin membrane. The maximum thickness of the face contact portion 220 is smaller than the minimum thickness of the support portion 230. Preferably, the thickness of the face contact portion 220 may be within the range of 0.3-1.5 mm. Experiment results show that a better sealing effect is obtained when the thickness of the face contact portion 220 is preferably within this scope. More preferably, the thickness of the face contact portion 220 may be within the range of 0.3-0.6 mm, and a better sealing effect is obtained when the thickness of the face contact portion 220 is within this scope. Optimally, the thickness of the face contact portion 220 may be 0.4 mm. The thin membrane may have a uniform thickness. However, the thickness of the thin membrane varies with different areas. For example, the thickness of the thin membrane in majority of the areas may be 0.6 mm, while in the stress sensitive areas such as the bridge of the nose (namely in the upper area A), the thickness of the thin membrane may be relatively small, for example 0.4 mm.

Figure 5:
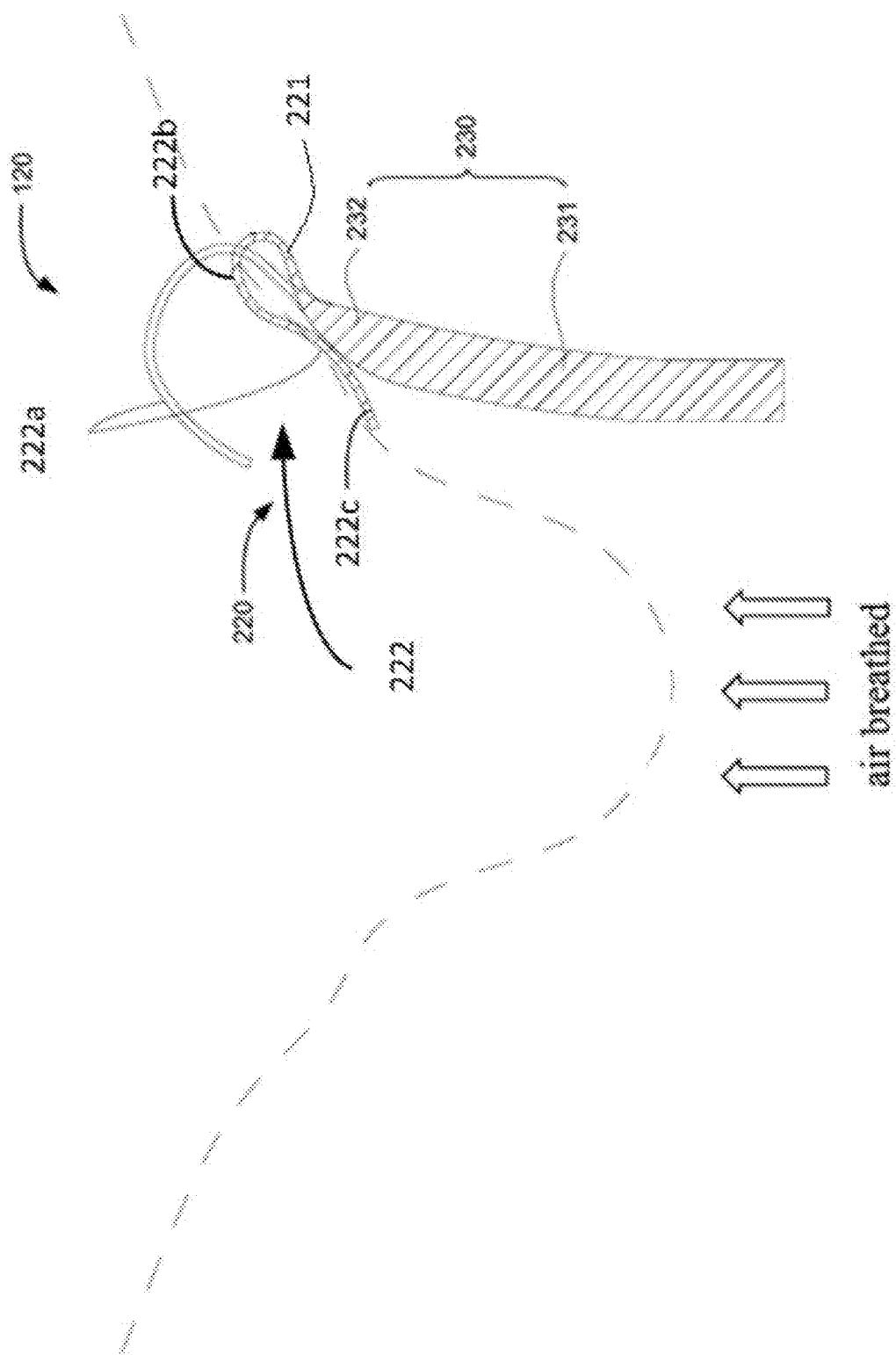
FIG. 5 is a sectional view where the cushion in FIG. 4 is in contact with the face of a patient when in use.

The face contact portion 220 includes an outwardly extending portion 221 and an inwardly extending portion 222 in at least a partial area, as shown in FIG. 4. The outwardly extending portion 221 extends from the support portion 230 towards the exterior of the cushion 120. The inwardly extending portion 222 extends from the outer circumference of the outwardly extending portion 221 toward the interior of the cushion 120. At least, the partial area mentioned above may include the middle area C. Preferably, the face contact portion 220 in the middle area C extends toward the exterior of the cushion 120 from the support portion 230. FIG. 4 to FIG. 5 relatively clearly illustrates the extension toward the side indicated by the arrow W; next, the face contact portion 220 bends toward the interior of the cushion 120 (the side indicated by the arrow N), thus forming the outwardly extending portion 221 and the inwardly extending portion 222. Within the cross section (namely the cross section as shown in FIG. 4-5) of the central line P-P of the cushion 120, preferably, the support portion 230 may approximately linearly extend, for example, along the shape of the nose. In this group of embodiments, the face contact portion 220 and the support portion 230 are hook-shaped in the cross section. The support portion of other structures will be described later.

The inwardly extending portion 222 has a high point 222a, as shown in FIG. 5. In actual application, when the face contact portion 220 gets in contact with the face of the patient (specifically, the two cheeks), the high point 222a, relative to the face, of the face contact portion 220 is in contact with the face first. Refer to FIG. 5. FIG. 5 illustrates a schematic view of the face contact portion 220 before and after the face contact portion 220 gets in contact with the face of the patient during use, wherein the dotted line represents the profile of the face of the patient, the full line which is filled in with a shadow line shows the state after the face contact portion 220 is in contact with the face of the patient, and the full line without the shadow line shows the natural state where the face contact portion 220 is not in contact with the face of the patient. As shown in FIG. 5, the high point 222a of the face contact portion 220 is positioned on one side where the face contact portion 220 faces the face of the patient. The high point 222a is first in contact with the face of the patient; after being extruded by the face, the face contact portion 220 deforms; then, the high point 222a gradually approaches the upper part of the support portion 230, and finally is pressed against the upper part of the support portion 230. Therefore, the high point 222a may also be called a pressed point. The support portion 230 has a support role, and the face contact portion 220 can well maintain the deformed state and forms a sealing point at the high point 222a. Besides, taking the high point 222a as the boundary, the inwardly extending portion 222 is divided into two parts, namely a first inwardly extending portion 222b which is connected with the outwardly extending portion 221, and a second inwardly extending portion 222c which is connected to the first inwardly extending portion 222b, as shown in FIG. 5. The first inwardly extending portion 222b extends from the high point 222a to the outwardly extending portion 221. The second inwardly extending portion 222c extends from the high point 222a to the free end of the face contact portion 220. When a breathing mask with the cushion 120 is fixed on the face of the patient and performs ventilation, the air breathed is sent into the nose or the oral and nasal cavities of the patient along the direction indicated by the arrow as shown in FIG. 5. The face contact portion 220 is made of a thin membrane, so by the effect of the face of the patient, the second inwardly extending portion 222c warps towards the face of the patient when receiving the air pressure, and the second inwardly extending portion 222c can go well with the face shape of the patient and is in contact with the face of the patient to form a firm first sealing area. Before the high point 222a is fitted with and pressed against the upper part of the support portion 230, the area surrounded by the outwardly extending portion 221 and the first inwardly extending portion 222b may be filled in with positive pressure air; when the high point 222a is fitted with and pressed against the upper part of the support portion 230, the first inwardly extending portion 222b and the outwardly extending portion 223 already form a sealed airbag. The face contact portion 220 is made of a thin membrane, so when stressed by the pressure of the positive pressure air therein, the airbag drives the first inwardly extending portion 222b gets in contact with and seals the face of the patient, thus forming a firm second sealing area. Firm sealing is achieved by the effects of the above mentioned sealing point, the first sealing area and the second sealing area.

Actually, the movement of the breathing mask in use is a main factor that results in damage to the sealing. In this embodiment of the disclosure, in the cheek areas which are not sensitive to pressure, the face contact portion 220 is pressed against the support portion 230 which plays the support role to apply a proper support force. In this way, on the one hand, the influences caused by the shape of the face contact portion 220 which is formed by the thin membrane can be reduced; on the other hand, the sealing point may be formed at the pressed point, and two sealing areas are formed on two sides of the pressed point, thus ensuring the firm sealing state. Besides, along the circumference of the cushion 120, the face contact portion 220 may also be basically positioned by virtue of other support points, even if the support portion 230 fails to provide effective support to the face contact portion 220 at some positions (for example in some uneven areas of the face of the patient). Moreover, the face contact portion 220 is made of the thin membrane, so the face contact portion 220 can be pressed towards the face of the patient by the effects of the gas pressure in the patient cavity to fill in some uneven areas. Therefore, reliable sealing can still be obtained. Therefore, in comparison with the prior art, the required support force in this embodiment of the disclosure may be smaller while the same sealing effect is achieved. On the other hand, when the support portion 230 which plays the support role deforms when receiving an external force (for example the external force caused by movement of the patient body or dragging of the ventilation pipe), the sealing effect of the face contact portion 220 is not greatly affected. This is because of the buffering effect of the outwardly extending portion 223 which forms the airbag, the relative movement between the support portion 230 and the face contact portion 220 usually occurs instead of the relative movement between the face contact portion 220 and the face of the patient, thus improving the sealing effectiveness. Therefore, the cushion provided by the embodiment of the disclosure has a relatively high anti-movement performance.

As mentioned above, the support is mainly executed in check areas which are not very sensitive to the pressure. The key is to realize reliable support and sealing in the middle area C of the cushion 120. The face contact portion 220 in the upper area A and the lower area B may have a structure similar to the middle area C, and may employ other structures which are commonly used in the prior art.

In a preferable embodiment of the disclosure, the support portion 230 may include a pressure support portion 231 and a contact support portion 232 that are connected mutually. Refer to FIG. 2, FIG. 4 and FIG. 5. The pressure support portion 231 is connected to the connection portion 210. The pressure support portion 231 plays a role of forming the patient cavity and maintaining the overall shape of the cushion 120, and provides reliable support to the face contact portion 220 in the middle area C, so the minimum thickness of the pressure support portion 231 is greater than the maximum thickness of the face contact portion 220. Besides, the pressure support portion 231 also needs a certain pressure adjusting capability, and in terms of cost, the pressure support portion 231 is better not very thick. Preferably, the thickness of the pressure support portion 231 may be within the range of 1.5-8 mm. When the thickness is within this range, the pressure support portion 231 has a good shape maintaining and supporting capability, and through its own elasticity, has a certain pressure adjusting capability. More preferably, the thickness of the pressure support portion 231 is within the range of 2-4 mm such that all capabilities of the pressure support portion 231 are comprehensively maintained on the optional level. Optimally, the thickness of the pressure support portion 231 is 3 mm. The contact support portion 232 is connected between the pressure support portion 231 and the face contact portion 220. The contact support portion 232 is positioned at the upper part of the support portion 230. The contact support portion 232 is a transition portion between the pressure support portion 231 and the face contact portion 220. The thickness of the contact support portion 232 gradually transits from the thickness of the pressure support portion 231 to the thickness of the face contact portion 220. Preferably, by the effect of the face of the patient, the face contact portion 220 is extruded by the face and then pressed against the contact support portion 232. In this way, the contact support portion 232 as a transition portion cannot only support the high point 222a, forms a firm sealing point between the high point 222a and the face of the patient, but also has relatively high elasticity because the thickness decreases gradually, and does not impose an uncomfortable pressing feeling on the face of the patient.

Preferably, the longitudinal extension lengths (namely the length along the central line P-P) of the pressure support portion 231 in the upper area A and the lower area B are both smaller than the longitudinal extension length of the pressure support portion 231 in the middle area C, which is preferably shown in FIG. 2. As mentioned above, the support portion 230 needs pressing against the cheeks of the patient in the middle area C, so the central line of the pressure support portion 231 has a relatively large extension length in the middle area C. A relatively small contact stress is required in the upper area A which contacts the bridge of nose that is relatively sensitive to stress and in the lower area B which is in contact with the upper lip/lower lip that is relatively sensitive to stress. Therefore, the central line of the pressure support portion 231 has a relatively short extension length in those two areas. During the actual treatment process, when the patient wears the breathing mask with the cushion 120, the whole cushion 120 is in the upper area A and the lower area B, and the face contact portion 220 does not come in contact with the support portion 230 or exactly contacts the support portion 230. In this way, the sensitive areas of the patient's face are relatively less stressed, and the maximum level of comfort is obtained.

Preferably, the pressure support portion 231 inclines towards the exterior of the cushion 120 along the direction from the connection portion 210 to the face contact portion 220, as shown in FIG. 2 and FIG. 4. In this way, the contact support portion 232 provides support to a larger area of the face of the patient, to reduce compression on the face. Besides, the whole support portion 230 has a certain pressure adjusting capability. The inclined pressure support portion 231 can also provide a patient cavity with a proper space. The patient cavity can accommodate the nose and/or mouth of the patient, and can provide a proper ventilation space for breathing by the patient. In a further preferable embodiment, the inclination angle (namely the complementary angle of the angle α in FIG. 4) of the pressure support portion 231 is within the range of 3-15 degrees with respect to the central line P-P of the cushion 120. When the inclination angle is within this range, the comprehensive effect of the above factors is optimum. It should be noted that, on the cross section along the central line P-P of the cushion 120 (namely the cross section as shown in FIG. 4), the inclination angle of the pressure support portion 231 may be a fixed value within the above preferable range with respect to the longitudinal direction (extension direction of the central line P-P) of the cushion 120, and may also be a variable within the above preferable range.

In a preferable embodiment of the disclosure, the internal circumferential surface (namely the internal surface of the dotted-line area that faces the cushion 120 in FIG. 4) of the contact support portion 232 may also be inclined towards the exterior of the cushion 120 along the direction from the connection portion 210 to the face contact portion 220, namely inclining toward the side indicated by the arrow W. In this way, the area of the contact support portion 232 that is in contact with the face of the patient may be greatly increased, thereby improving the wearing level of comfort of the patient. The internal circumferential surface is a plane or a curved face. When the internal circumferential surface is a curved face, the internal circumferential surface may be designed as a curved face that fits the face profile of the patient. When the internal circumferential surface of the contact support portion 232 inclines toward the exterior and the matched pressure support portion 231 also inclines toward the exterior, a firm seal is achieved when the cushion is used, and a relatively large support area is obtained. By the effect of the acting force in the same unit, the stressed feeling is not obvious, thus improving the level of sealing comfort.

Further, on the cross section along the central line P-P of the cushion 120 (namely the cross section as shown in FIG. 4), the internal circumferential surface of the contact support portion 232 may be a circular bead which projects toward the interior of the cushion 120. The internal circumferential surface of the contact support portion 232 projects towards the interior of the cushion 120 such that the circle dot corresponding to the internal circumferential surface is positioned on the exterior of the cushion 120. In this way, the contact support portion 232 has a relatively large area that fits the face profile of the patient, and has the high point 211 reliably supported, thus integrating the comfort level and sealing.

Figures 6A, 6B:
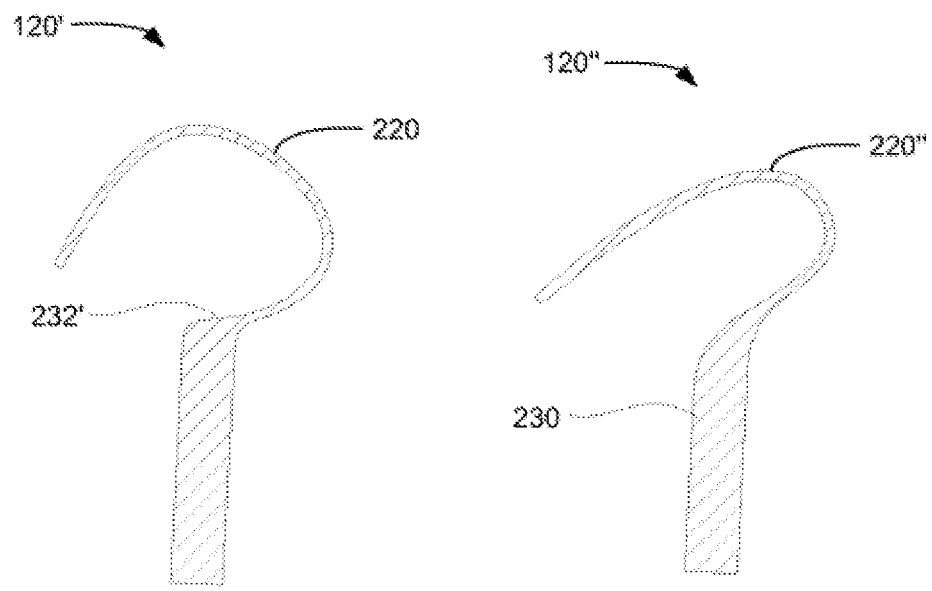
FIG. 6a-6c are partial sectional views of a cushion in one embodiment in the first group of embodiments according to the disclosure.

In addition, preferably, as shown in FIG. 6a, a preferable cushion 120' in another embodiment according to the disclosure is provided. The components in FIG. 6a that are identical or similar with those in FIG. 2 to FIG. 5 are marked with the same marks, and the identical or similar parts are not described in detail in this embodiment of the disclosure. The cushion 120' is different from the cushion 120 in the contact support portion 232'. As shown in FIG. 6a, the internal circumferential surface of the contact support portion 232' that faces the interior of the cushion 120 extends along the transverse direction of the cushion 120 (the direction vertical to the central line P-P). As shown in FIG. 6a, the internal circumferential surface of the contact support portion 232' extends along the approximately horizontal direction. Replacing the inclined face or inclined curved face in the above embodiment with such a small plane may make the stress on the face contact portion 220 more reliable.

Figure 6C:
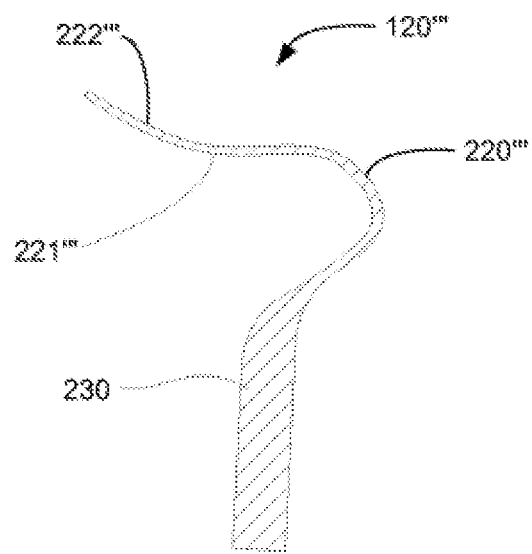

Besides, FIG. 6b and FIG. 6c also illustrate another two preferable cushions 120" and 200'''. The cushions 120" and 200''' are basically the same as the cushion 120, except the face contact portions 220" and 220''' thereof. The face contact portion 220" is transformed into that a portion facing the face of the patient which is relatively smooth and has no obvious protruding high point. When the face of the patient is in contact with the face contact portion 220", the face is in contact with the face contact portion 220" in a certain area at the same time, but the technical effect as mentioned above can also be achieved. In the face contact portion 200''', the part of an inwardly extending portion 222''' that is positioned on the inner side of a pressed point 221" is partly bent (upward) toward one side away from the support portion 230. In this way, when a patient wears a breathing mask with the cushion 120''', the membrane structure of the inwardly extending portion 222''' may more tightly fit the face of the patient. The other components of the cushions 120" and 120,''' for example the support portion 230, are identical with those in the above embodiments and therefore are not repeatedly described. The above mentioned structures of the face contact portion 220" and 220" may be used in combination with various embodiments as mentioned in the disclosure. Those skilled in the art may select the shapes and structures of the fact contact portion and the face support portion upon demand.

As shown in FIG. 2. FIG. 4 and FIG. 7, the connection portion 210 may include a connection section 211 and a bent section 212. The connection section 211 is used for connecting to the breathing mask, and specifically, connected to the frame 110 (see FIG. 1) of the breathing mask. The transverse size of the connection section 211 is smaller than the transverse size of the support portion 230. The transverse size of a certain component refers to the distance from the component to the central line P-P. The transverse size of the connection section 211 refers to the distance from the connection section 211 to the central line P-P, and the transverse size of the support portion 230 refers to the distance from the support portion 230 to the central line P-P. The transverse size of the connection section 211 is smaller than the transverse size of the support portion 230, so the connection section 211 is positioned on the inner side of the support portion 230 in the transverse direction. The bent section 212 is connected between the connection section 211 and the support portion 230. The support portion 230 is formed with a protruding platform at the bottom. The bent section 212 may also extend along the approximately transverse direction of the cushion 120, and may extend along the direction which forms a certain angle with the transverse direction. By the effect of the bent section 212, the stressed height of the support portion 230 may be adjusted freely, providing a bigger self-adapted space when the patient wears the breathing mask, and further improving the wearing comfort level. Preferably, the bent section 212 extends along the transverse direction of the cushion 120. In this way, when the stressed height of the support portion 230 is adjusted, the support portion 230 has a relatively large adjustment allowance in two directions along the central line P-P.

Further preferably, the transverse widths of the bent section 212 in the upper area A and in the lower area B are both greater than the transverse width of the bent section 212 in the middle area C, which is preferably shown in FIG. 2. The transverse width of the bent section 212 refers to the extension length D of the bent section 212 in the transverse direction. See FIG. 4. The areas corresponding to the bridge of the nose and the upper lip/lower lip are stress sensitive areas. In those two areas, the support force applied by the support portion 230 to the face contact portion 220 can be well adjusted if the bent section 212 has a relatively large transverse width, thus avoiding the support portion 230 to directly act on the bridge of the nose and the upper lip/lower lip of the patient and to result in poor comfort level. Further preferably, the transverse width of the bent section 212 gradually decreases from the upper area A and from the lower area B to the middle area C. In this way, the adjusting capability of the bent section 212 gradually decreases from the upper area A and from the lower area B to the middle area C, and at a certain position in the middle area C, the transverse width of the bent section 212 has gradually decreased to be equal to or approximately equal to zero. In the area where the bent section 212 has a smaller transverse width, the acting face provided by the support portion 230 more directly apply to the face contact portion 220, so the face contact portion 220 may be well supported at the cheeks. Therefore, when the patient moves his/her body, for example turns over during sleep, the mask wearing stability is enhanced, the stress on the sensitive areas of the face is reduced, and the wearing comfort level is improved.

In a preferable embodiment of the disclosure, the maximum transverse width of the bent section 212 in the upper area A is within the range of 3-8 mm. More preferably, the maximum transverse width of the bent section 212 in the upper area A is within the range of 5-7 mm. Optimally, the maximum transverse width of the bent section 212 in the upper area A is 6 mm. In another preferable embodiment of the disclosure, the maximum transverse width of the bent section 212 in the lower area B is within the range of 2-7 mm. More preferably, the maximum transverse width of the bent section 212 in the lower area B is within the range of 4-6 mm. Optimally, the maximum transverse width of the bent section 212 in the lower area B is 5 mm. Considering that the bridge of the nose is more sensitive than the upper lip and lower lip, during the process of designing the cushion 120, the maximum transverse width of the bent section 212 in the upper area A may be greater than the maximum transverse width in the lower area B such that the portion at the bridge of the nose has a relatively high stress adjusting capability. Of course, the maximum transverse width selected from the above preferable range can all achieve the objectives of the disclosure and achieve an ideal effect. In another preferable embodiment, the thickness of the bent section 212 may be within the range of 0.4-2 mm, preferably within the range of 0.7-1.8 mm, further preferably within the range of 1.0-1.4 mm, and optimally 1.2 mm. Experiments show that the thickness of the bent section 212 selected from the more preferable range achieves a better effect.

In the first group of embodiments, the contact support portion 232 of the support portion 230 is a single-layer structure. The following is the description of the laminated contact support portion 1232 in the second group of the embodiment, as shown in FIG. 9-12. The components that are identical or similar to those in the first group of embodiments are marked with the same marks, and the identical or similar parts are not described in detail in the disclosure. The cushion 1120 as shown in FIG. 9-12 is different from the cushion 120 in the support portion 1230, and the support portion 1230 may include a pressure support portion 1231 and a contact support portion 1232. The difference is mainly focused at the contact support portion 1232.

Figure 9:
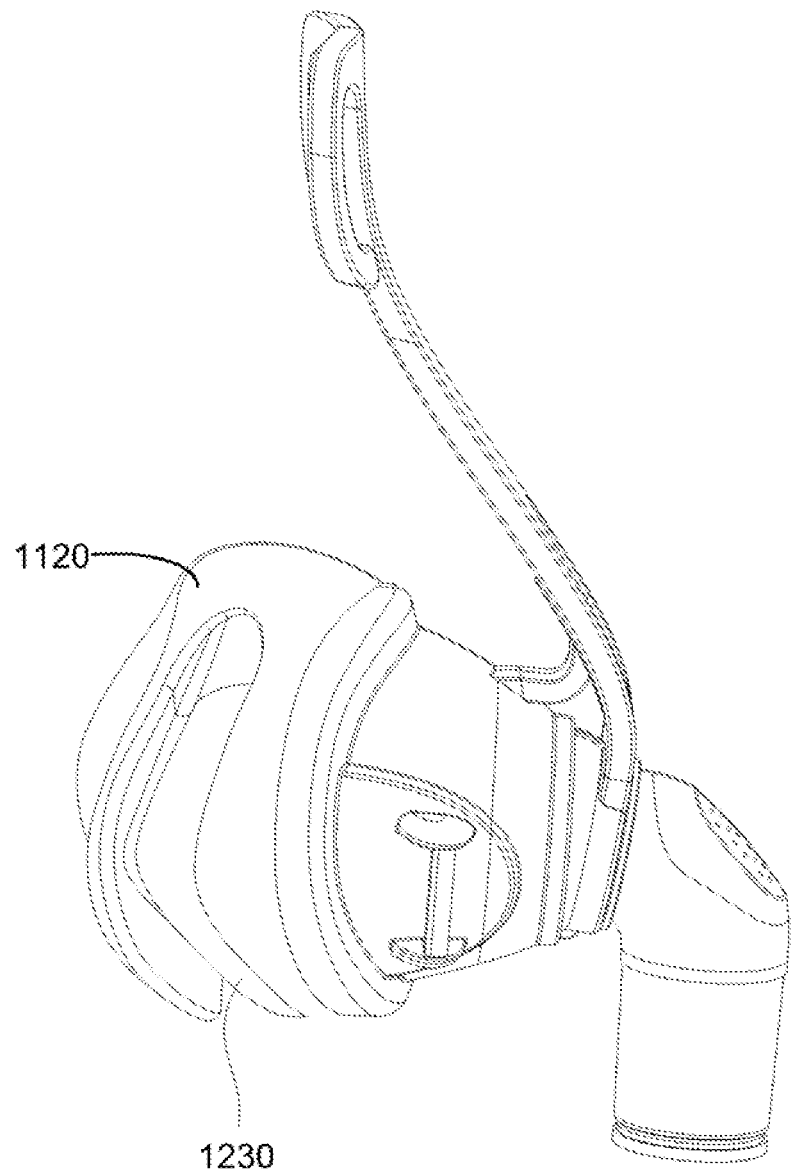
FIG. 9 is a three-dimensional view of a breathing mask in the second group of embodiments according to the disclosure.
Figure 10:
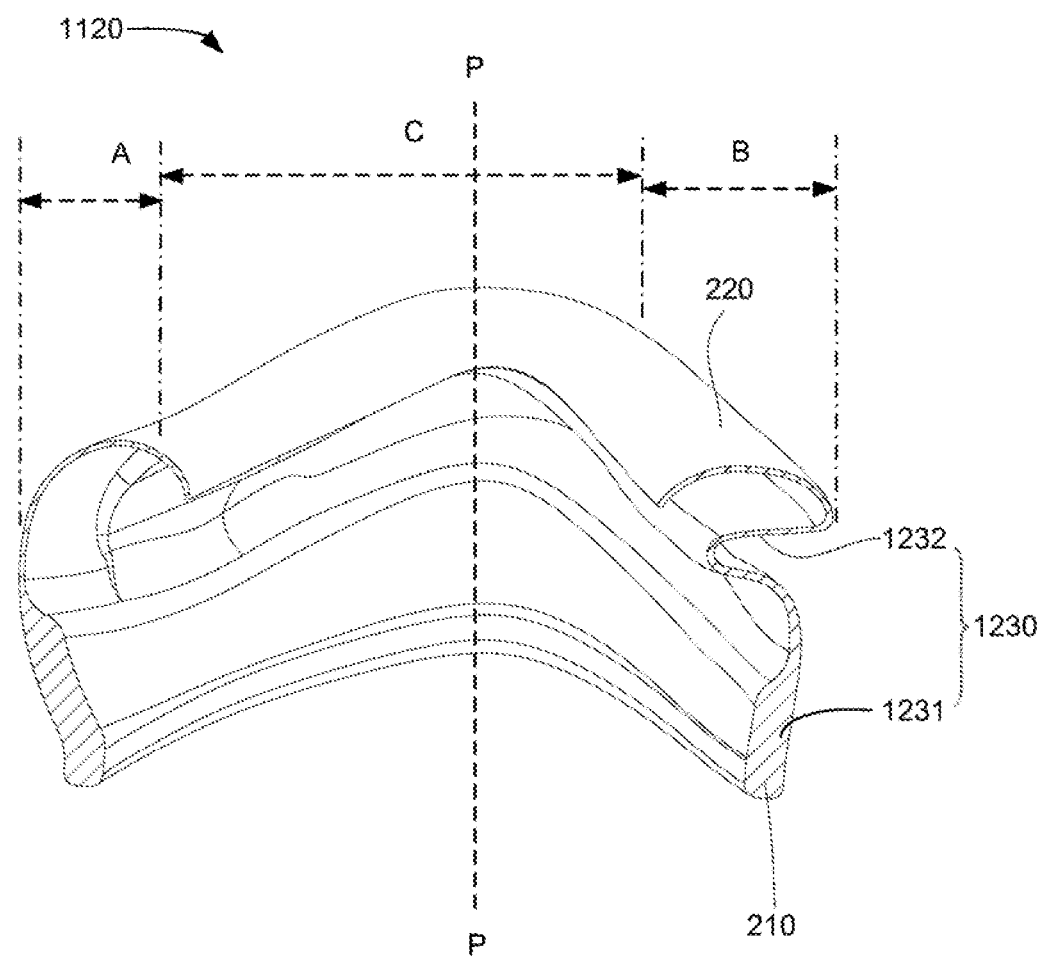
FIG. 10 is a sectional view of a cushion in the second group of embodiments according to the disclosure.
Figure 11:
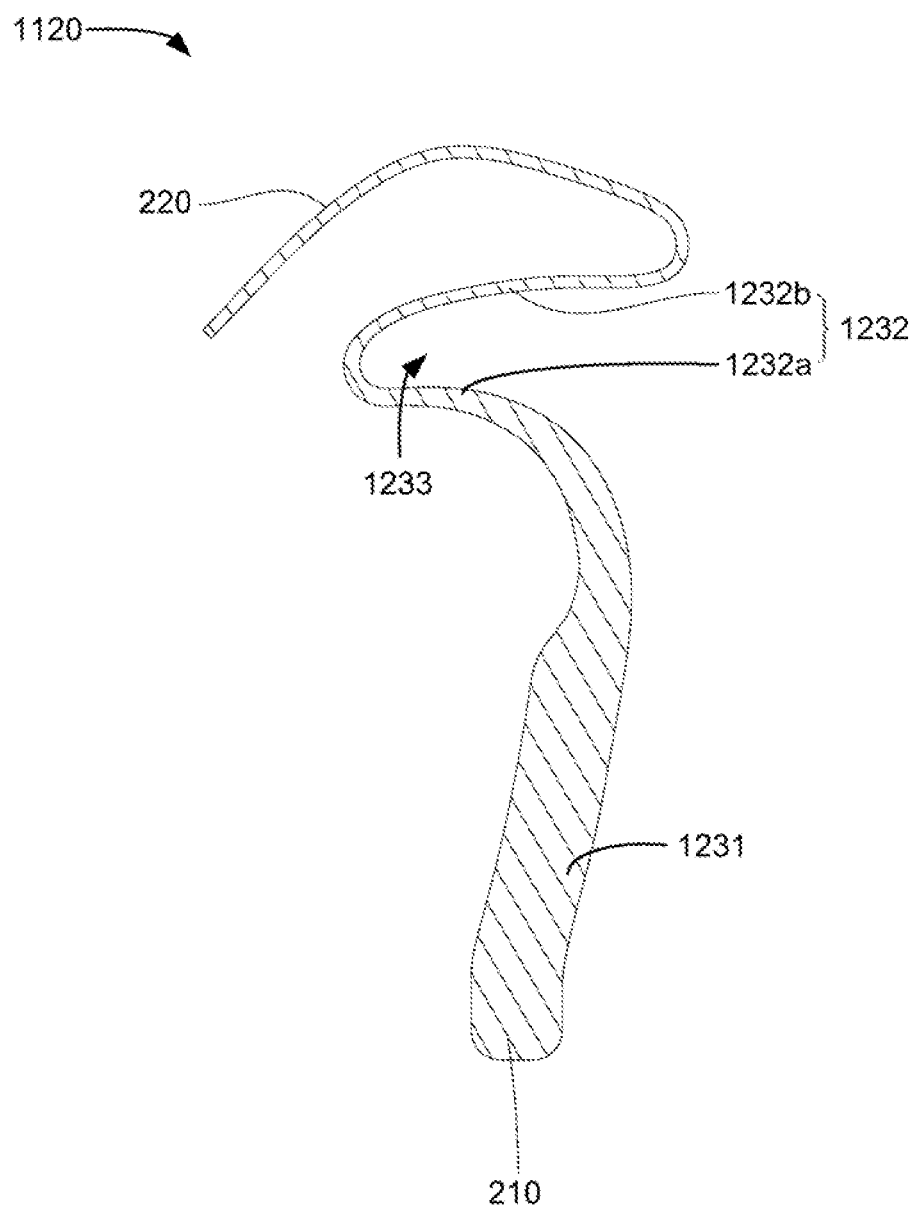
FIG. 11 is a sectional view of the cushion in the sectional view 9-10 along the direction similar to the arrow M as shown in FIG. 3; and, FIG. 12 is a sectional view where the cushion in FIG. 11 is in contact with the face of a patient during use.

The contact support portion 1232 has a laminated structure in at least a partial area, as shown in FIG. 10-11. For example, the contact support portion 1232 has the laminated structure in the middle area C and in the lower area B, and has a single-layer structure which is identical with that in the first group of embodiments or prior art in the upper area A. The laminated contact support portion 1232 may include a first contact support portion 1232*a* and a second contact support portion 1232*b*, as shown in FIG. 11-12. The first contact support portion 1232*a* extends towards the interior of the cushion 1120 from the pressure support portion 1231, forming a first bend. The second contact portion 1232*b* extends toward the exterior of the cushion 1120 from the first contact support portion 1232*a* to the face contact portion 220, forming a groove 1233, namely a second bent, between the first contact support portion 1232*a* and the second contact support portion 1232*b*. As mentioned above, the face contact portion 220 extends outward first and then inward, forming a third bend. Therefore, in the cross section a shown in FIG. 9, the contact support portion 1232 and the face contact portion 220 form an approximately S shape. The laminated contact support portion 1232 plays the role of supporting the face contact portion 220 in use. The face contact portion 220, similar to that in the first group of embodiments, includes an outwardly extending portion 221 and an inwardly extending portion 222. The outwardly extending portion 221 extends towards the exterior of the cushion from the external circumference of the second contact support portion 1232*b*, and the pressed point is positioned on the second contact support portion 1232*b*.

In this way, when the breathing mask fixed on the face of the patient performs ventilating, the front face of the face contact portion 220 receives an air pressure and can tightly fit the face of the patient to form a seal, while the rear face of the face contact portion 220 tightly fits a laminated layer which is formed by laminating the first contact support portion 1232*a* and the second contact support portion 1232*b* together, to first form a sealing point similar to that in the first group of embodiments, and then form two sealing areas on the inner side and outer side of the sealing point. Therefore, a more stable sealing effect is obtained when the patient wears the mask, and a gas leak is prevented. Therefore in comparison with the prior art, a smaller support force is required while the same sealing effect is obtained. On the other hand, when the support portion 1230 is deformed when receiving an external force, for example, a movement of the body of the patient, dragging of the ventilation pipe, etc., the laminated contact support portion 1232 can absorb the external force to a larger extent to deform, while no relative movement occurs between the face contact portion 220 and the face of the patient, thus improving the effectiveness of the sealing. Therefore, the second group of embodiments features higher anti-movement performance. In addition, the laminated structure with the groove forms an elastic support with a certain height in use. When the headgear is tightened, the support portion 1230 has a relatively large elastic movement space such that the stress on the face contact portion 220 is not obvious, improving the wearing feeling. The face contact portion 220 is pressed against the laminated structure, so the contact area is relatively large, and the patient feels more comfortable and achieves a better sealing effect when wearing the breathing mask. Moreover, in comparison with the above mentioned single-layer structure, the laminated structure has a higher elastic deformation capability.

Preferably, in the cross section as shown in FIG. 11, the groove 1233 gradually opens towards the exterior of the cushion 1120, and the groove 1233 with a shape of, for example, a flare opening, is more suitable for sealing and molding. In the embodiment as shown in the drawings, the groove 1233 is mainly formed in the middle area C (namely the face contact area) and the lower area (namely the area that is in contact with the upper lip or lower lip) 13. Optionally, the groove may also be individually distributed in the middle area C. The upper area A (namely the area that is in contact with the bridge of the nose) is preferably free of the groove support, so that the face contact area 220 and the support portion 1230 are integrally hook-shaped to reduce stress on the bridge of the nose. In addition, the magnitude of the support force supplied by the groove 1233 can be controlled through the shape and height (the size along the extension direction of the central line P-P, as shown in FIG. 10) and the thickness of the first contact support portion 1232*a* and the second contact support portion 1232*b*. In this way, the support portion can be distributed to different areas of the face contact portion under control. For example, in the upper area and in the lower area, the groove may provide a smaller support force to reduce irritation on the bridge of the nose, and the upper lip/lower lip, and the support force can be slightly increased in the face area with insensitive region to ensure the sealing force of the cushion. Besides, in order to control the pressure distribution in different areas of the face, the height of the pressure support portion 1231 may also be adjusted as mentioned above (the size along the extension direction of the central line P-P, as shown in FIG. 10). For example, the height of the pressure support portion 1231 in the upper area A and in the lower area B may be smaller than the height in the middle area C.

Preferably, the second contact support portion 1232*b* may be formed by a thin membrane, like the face contact portion 220. The thickness of the second contact support portion 1232*b* may be within the range of 0.3-1.5 mm, preferably within the range of 0.3-0.6 mm, and more preferably 0.4 mm. The thickness of the second contact support portion 1232*b* may be consistent with the thickness of the face contact portion 220. The thickness of the first contact support portion 1232*a* is greater than the thickness of the second contact support portion 1232*b*, the first contact support portion 1232*a* becomes thinner gradually along the extension direction from the pressure support portion 1231 to the second contact support portion 1232*b*. The thickness of the first contact support portion 1232*a* may be within the range of 0.5-1.2 mm, preferably 0.6 mm. Among the two portions, the first contact support portion 1232*a* mainly plays a support role, so the first contact support portion 1232*a* may have different thicknesses in different areas, for example the thickness in the middle area C may be greater than the thickness in the upper area A and in the lower area B. The second contact support portion 1232*b* is a thin membrane, and the first contact support portion 1232*a* is thinner when getting closer to the second contact support portion 1232*b*, so the second contact support portion 1232*b* can fit the first contact support portion 1232*a* in use, and the two form a curved-face support that projects toward the face of the patient. Therefore, the wearing is more conformable.

Preferably, in the cross section as shown in FIG. 9, the second contact support portion 1232*b* is circularly bent from the first contact support portion 1232*a*. The bottom of the groove 1233 is shaped like a circular bead to enhance the elastic deformation capability of the contact support portion 1232. Preferably, the radius of curvature of the circular bead may be within the range of 0.2-2 mm.

The disclosure also provides a breathing mask. The breathing mask may include any one of the frames and any one of the cushions as mentioned above. The cushion is connected to the frame through the connection portion. The cushion and the frame together form the patient cavity which accommodates the mouth and/or nose. For all components and structures of the cushion and the frame, refer to the descriptions of corresponding parts in the text above.

The disclosure is described with the above embodiments, but it should be understood that the above embodiments are provided for the purpose of illustration and description instead of limiting the disclosure in the range of the described embodiments. Those skilled in the art may understand that the disclosure is not limited to the above embodiments, and may achieve various changes and modifications on the basis of the disclosure, and those changes and modifications should all fall within the protective scope of the disclosure. The protective scope of the disclosure is defined by the attached claims and equivalent scopes thereof.

What is claimed is:

1. A cushion for a breathing mask, wherein the cushion comprises:
    a connection portion for connecting to a frame or an elbow assembly of the breathing mask;
    a face contact portion configured to contact a face of a patient, wherein the face contact portion is formed by a membrane; and,
    a support portion connected between the connection portion and the face contact portion,
    the support portion comprises a pressure support portion and a contact support portion which are connected to each other;
    the pressure support portion is connected to the connection portion, the pressure support portion forms a patient cavity of the cushion;
    wherein the face contact portion has an outwardly extending portion and an inwardly extending portion, the outwardly extending portion extends from the support portion and extends away from the patient cavity;
    a maximum thickness of the face contact portion is smaller than a minimum thickness of the support portion; and wherein,
    the inwardly extending portion has a high point, the inwardly extending portion is divided into a first inwardly extending portion connected with the outwardly extending portion and a second inwardly extending portion connected with the first inwardly extending portion at the high point, wherein the high point serves as a boundary;
    the high point of the inwardly extending portion is configured to be pressed against the support portion in a response to pressing against the face of the patient;
    the first inwardly extending portion is configured to form at least a portion of a closed air bag, a sealing area is formed in the response to pressing against the face of the patient while the first inwardly extending portion is tightly in contact with and seals to the face of the patient;
    the second inwardly extending portion is configured to warp toward the face of the patient in the response to pressing against the face of the patient; and
    the first inwardly extending portion and the contact support portion form the closed air bag.

2. The cushion according to claim 1, wherein the contact support portion is connected to the face contact portion, the contact support portion is a transition portion between the pressure support portion and the face contact portion, and the face contact portion is configured to be pressed against the contact support portion in the response to pressing against the face of the patient.

3. The cushion according to claim 2, wherein the pressure support portion and/or the contact support portion inclines away from the patient cavity of the cushion along a direction from the connection portion to the face contact portion.

4. The cushion according to claim 3, wherein a longitudinal inclination angle of the pressure support portion is 3-15 degrees with respect to a central line of the cushion.

5. The cushion according to claim 2, wherein an internal circumferential surface of the contact support portion has a circular arc projecting towards an interior of the cushion.

6. The cushion according to claim 2, wherein the contact support portion comprises a first contact support portion and a second contact support portion in at least a particular area; the first contact support portion extends towards an interior of the cushion from the pressure support portion; and the second contact support portion extends towards an exterior of the cushion from the first contact support portion to the face contact portion, to form a groove between the first contact support portion and the second contact support portion.

7. The cushion according to claim 6, wherein the second contact portion is configured to be overlaid on the first contact support portion in the response to pressing against the face of the patient.

8. The cushion according to claim 6,
wherein the second contact support portion is formed by a membrane having a thickness;
wherein the first contact support portion comprises a thickness;
wherein the thickness of the second contact support portion or the thickness of the first contact support portion gradually decreases in an extension direction; and
wherein the thickness of the membrane of the second contact support portion is smaller than the thickness of the first contact support portion.

9. The cushion according to claim 6, wherein the groove gradually opens towards the exterior of the cushion.

10. The cushion according to claim 6, wherein the second contact support portion circularly bends from the first contact support portion such that a bottom of the groove is a circular bead.

11. The cushion according to claim 1, wherein the connection portion comprises
a connection section for connecting to the breathing mask, wherein a transverse size of the connection section is smaller than a transverse size of the support portion; and,
a bent section connected between the connection section and the support portion.

12. The cushion according to claim 11, wherein along the circumference direction of the cushion, the cushion comprises an upper area, a lower area, and a middle area connected between the upper area and the lower area, and a transverse width of the bent section gradually reduces from the upper area to the middle area and from the lower area to the middle area.

13. A breathing mask, comprising:
a frame, wherein a main body of the frame has an air supply opening for connecting to a bend tube; and,
a cushion connected to the frame through a connection portion;
wherein the cushion comprises:
a face contact portion configured to contact a face of a patient, wherein the face contact portion is formed by a membrane; and,
a support portion connected between the connection portion and the face contact portion, the support portion comprises a pressure support portion and a contact support portion which are connected to each other;
the pressure support portion is connected to the connection portion, the pressure support portion forms a patient cavity of the cushion;
wherein the face contact portion has an outwardly extending portion and an inwardly extending portion, the outwardly extending portion extends from the support portion and extends away from the patient cavity;
a maximum thickness of the face contact portion is smaller than a minimum thickness of the support portion; and wherein,
the inwardly extending portion has a high point, the inwardly extending portion is divided into a first inwardly extending portion connected with the outwardly extending portion and a second inwardly extending portion connected with the first inwardly extending portion at the high point, wherein the high point serves as a boundary;
the high point of the inwardly extending portion is configured to be pressed against the support portion in a response to pressing against the face of the patient;
the first inwardly extending portion is configured to form at least a portion of a closed air bag, a sealing area is formed in the response to pressing against the face of the patient while the first inwardly extending portion is tightly in contact with and seals to the face of the patient;
the second inwardly extending portion is configured to warp toward the face of the patient in the response to pressing against the face of the patient; and
the first inwardly extending portion and the contact support portion form the closed air bag.

14. The breathing mask according to claim 13, wherein the contact support portion is connected to the face contact portion, the contact support portion is a transition portion between the pressure support portion and the face contact portion, and the face contact portion is configured to be pressed against the contact support portion in the response to pressing against the face of the patient.

* * * * *